(12) United States Patent
Kawamura

(10) Patent No.: US 10,512,421 B2
(45) Date of Patent: Dec. 24, 2019

(54) PIEZOELECTRIC ELEMENT AND BEND DETECTING SENSOR

(71) Applicant: Murata Manufacturing Co., Ltd., Nagaokakyo-shi, Kyoto-fu (JP)

(72) Inventor: Hideki Kawamura, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 423 days.

(21) Appl. No.: 15/433,082

(22) Filed: Feb. 15, 2017

(65) Prior Publication Data

US 2017/0156636 A1 Jun. 8, 2017

Related U.S. Application Data

(63) Continuation of application No. PCT/JP2015/071060, filed on Jul. 24, 2015.

(30) Foreign Application Priority Data

Aug. 18, 2014 (JP) ................. 2014-165887

(51) Int. Cl.
| | | |
|---|---|---|
| *A61B 5/11* | (2006.01) | |
| *H01L 41/193* | (2006.01) | |
| *A61B 5/00* | (2006.01) | |
| *G01B 7/16* | (2006.01) | |
| *H01L 41/047* | (2006.01) | |

(Continued)

(52) U.S. Cl.
CPC ............ *A61B 5/11* (2013.01); *A61B 5/6824* (2013.01); *A61B 5/6831* (2013.01); *G01B 7/22* (2013.01); *H01L 41/0477* (2013.01); *H01L 41/0805* (2013.01); *H01L 41/1132* (2013.01); *H01L 41/193* (2013.01)

(58) Field of Classification Search
CPC .............. H01L 41/042; H01L 41/0477; H01L 41/0805; H01L 41/1132; H01L 41/193
See application file for complete search history.

(56) References Cited

U.S. PATENT DOCUMENTS 6,360,603 B1 3/2002 Tabota
9,429,749 B2 8/2016 Kawai
(Continued)

FOREIGN PATENT DOCUMENTS

JP H06-216422 A 8/1994
JP 2000-121661 A 4/2000
(Continued)

OTHER PUBLICATIONS

International Search Report issued for International Application No. PCT/JP2015/071060, dated Oct. 13, 2015.
(Continued)

*Primary Examiner* — Bryan P Gordon
(74) *Attorney, Agent, or Firm* — Arent Fox LLP

(57) ABSTRACT

A capacitor is coupled in parallel with a piezoelectric unit in a sensor. The piezoelectric unit is formed by a film which is sandwiched between a signal electrode and a reference potential electrode. A capacitor is formed by a dielectric film located between the signal electrode and a reference potential electrode. As a result, the capacitance of the sensor element is higher than it would be if the sensor only contained the piezoelectric unit.

20 Claims, 8 Drawing Sheets

(51) Int. Cl.
*H01L 41/08* (2006.01)
*H01L 41/113* (2006.01)

(56) References Cited

U.S. PATENT DOCUMENTS

| | | | | |
|---|---|---|---|---|
| 2004/0051422 A1* | 3/2004 | Kashiwaya | ......... | H01L 41/1875 310/324 |
| 2005/0046030 A1* | 3/2005 | Nakamura | ......... | H01L 41/0471 257/758 |
| 2009/0093722 A1* | 4/2009 | Takeuchi | ............. | B06B 1/0629 600/459 |
| 2013/0038174 A1* | 2/2013 | Kim | ...................... | H01L 41/053 310/327 |
| 2014/0185140 A1* | 7/2014 | Kawai | ................ | G02B 27/0006 359/508 |
| 2014/0331791 A1 | 11/2014 | Ishii et al. | | |
| 2015/0084487 A1* | 3/2015 | Mori | .................. | H01L 41/0472 310/364 |

FOREIGN PATENT DOCUMENTS

| | | |
|---|---|---|
| JP | 2002-315362 A | 10/2002 |
| JP | 2014-127998 A | 7/2014 |
| WO | WO 2013/111841 A1 | 8/2013 |

OTHER PUBLICATIONS

Written Opinion of the International Searching Authority issued for International Application No. PCT/JP2015/071060, dated Oct. 13, 2015.

Zhonghua Zhang et al.; "Influence of Multiple Piezoelectric Effects on Static Performance of Piezoelectric Sensors"; Piezoelectrics & Acoustooptics, vol. 31, No. 3, Jun. 2009, pp. 360-363, (Abstract is in English).

Chinese Office Action dated Jun. 12, 2018 and issued for Chinese Application No. 201580043966.6.

* cited by examiner

FIG. 2
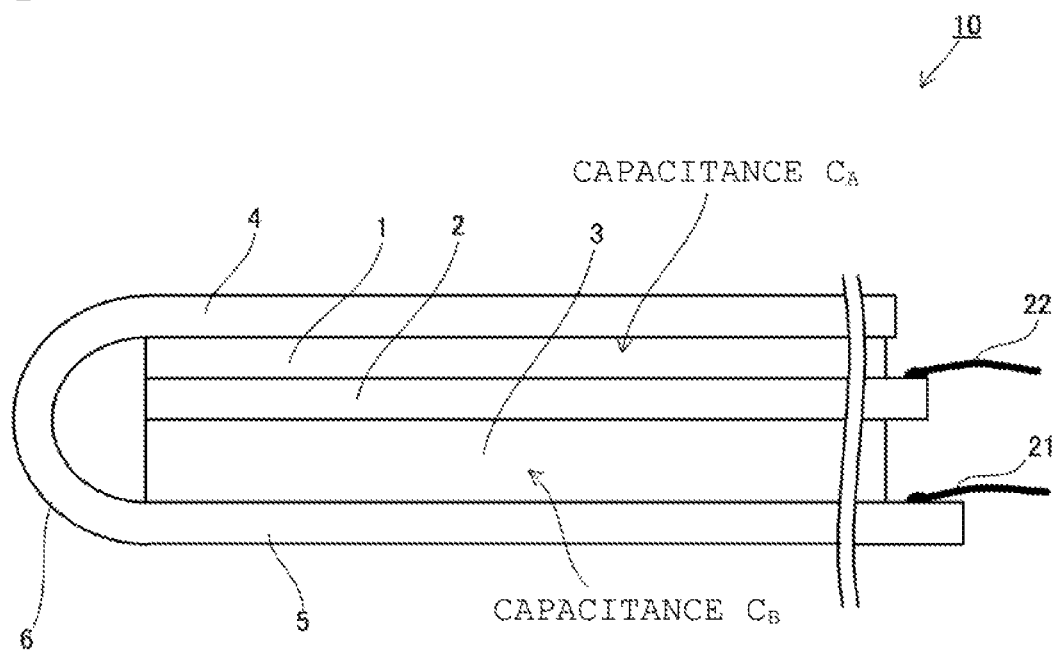
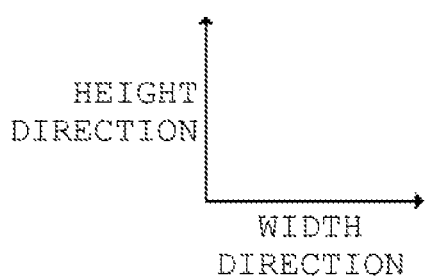

FIG. 4
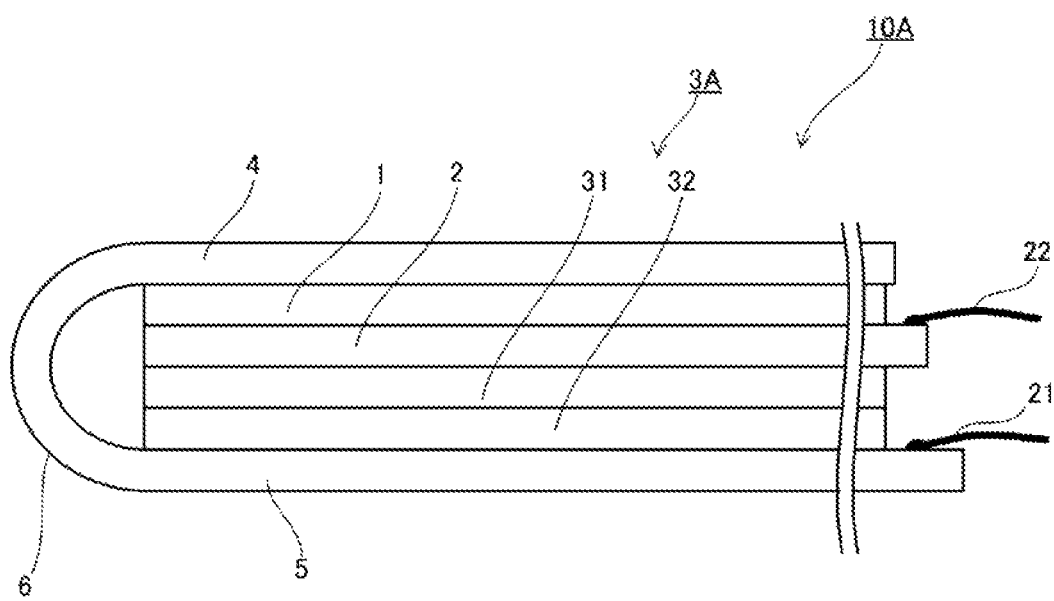
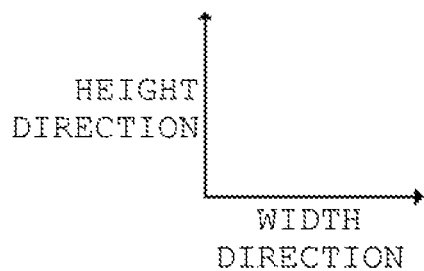

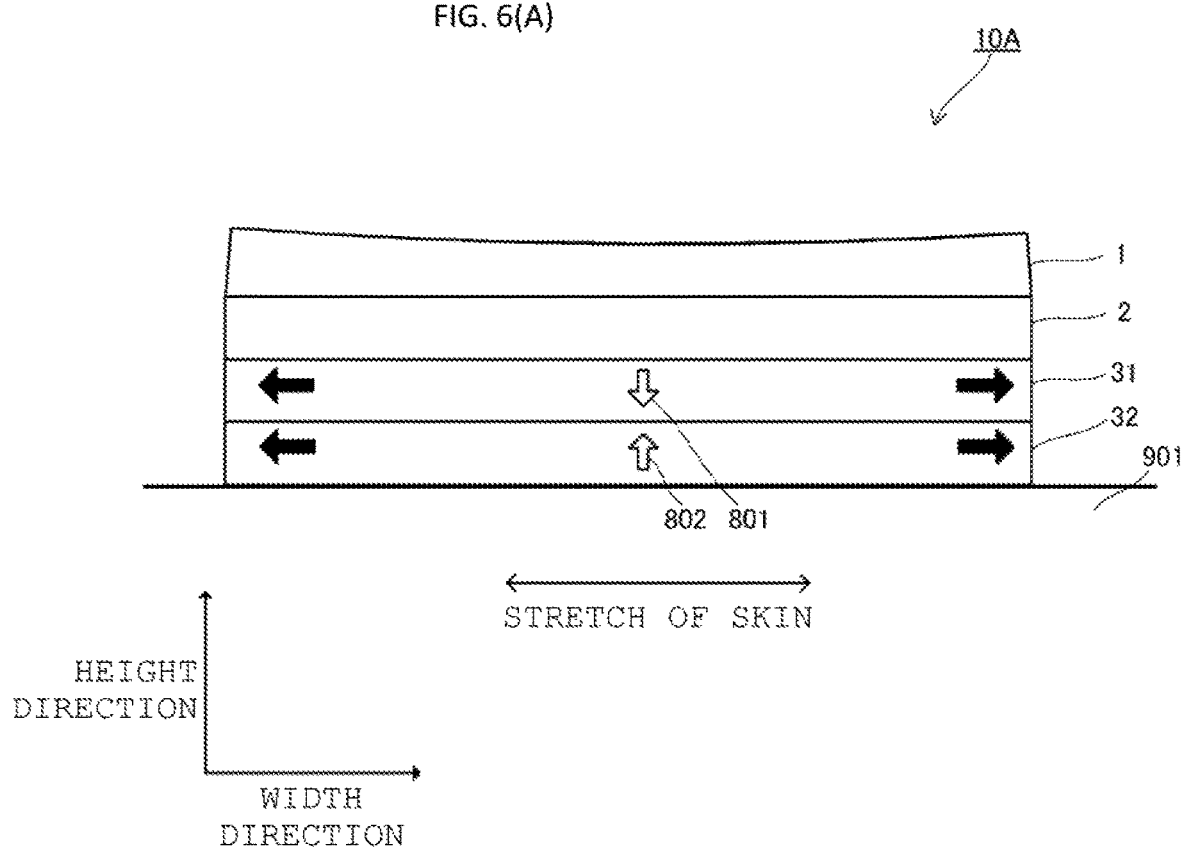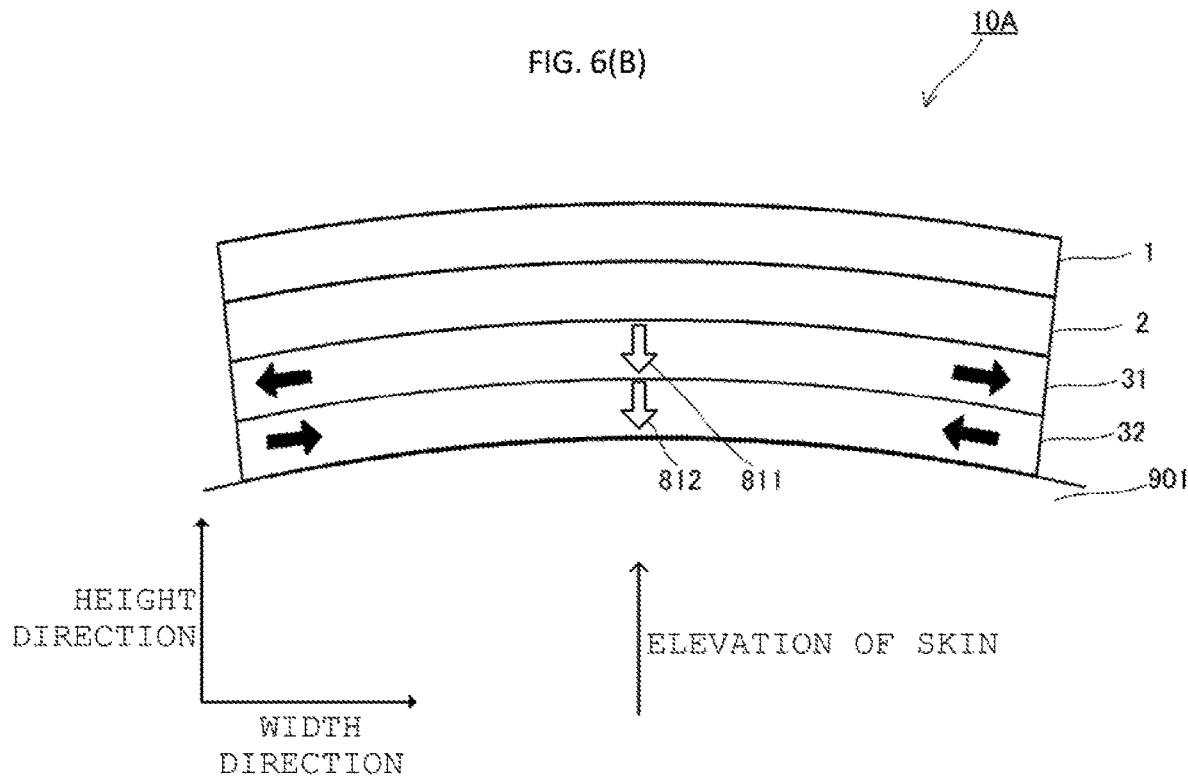

PIEZOELECTRIC ELEMENT AND BEND DETECTING SENSOR

CROSS REFERENCE TO RELATED APPLICATIONS

The present application is a continuation of International application No. PCT/JP2015/071060, filed on Jul. 24, 2015, which claims priority to Japanese Patent Application No. 2014-165887, filed on Aug. 18, 2014, the entire contents of each of which are incorporated herein by reference.

TECHNICAL FIELD

The present invention relates to a piezoelectric element which includes a film partially including a piezoelectric resin and sandwiched between electrodes.

BACKGROUND ART

In recent years, piezoelectric elements which each include a film (simply referred to as a piezoelectric film below) partially including, for example, polyvinylidene fluoride as piezoelectric resin and sandwiched between electrodes are known. For example, Japanese Patent Application Laid-Open No. H06-216422 discloses a piezoelectric element formed by disposing piezoelectric films made of polyvinylidene fluoride on opposite principal surfaces of electrodes, disposing two other electrodes on an outermost layer, and sandwiching each of the piezoelectric films between the electrodes.

Each piezoelectric film produces charges when the piezoelectric element is distorted, for example by being stretched and contracted in a predetermined direction. As each piezoelectric film produces charges, a potential difference is produced between the electrodes which sandwich each piezoelectric film. A voltage detection circuit detects the potential difference between the electrodes which sandwich each piezoelectric film thereby making it possible to detect that the piezoelectric element has been distorted. The potential difference between the electrodes which sandwich each piezoelectric film will be referred to simply as a voltage of the piezoelectric element below.

A piezoelectric resin has a relatively low dielectric constant ε (F/m) compared to that of piezoelectric ceramics and produces a low capacitance. When the piezoelectric element disclosed in the foregoing application is directly connected to a voltage detection circuit, the causes following problems to occur.

First, a voltage produced in the piezoelectric element becomes too high, and when, for example, it exceeds a drive voltage of the voltage detection circuit, it is difficult to precisely detect an output voltage from the piezoelectric element. Second, because a capacitance of the piezoelectric element is low, the voltage of the piezoelectric element is significantly influenced by noise superimposed on the charges generated by the piezoelectric film. Third, because the capacitance of the piezoelectric element is low, a time constant becomes low and the charges quickly dissipate from the piezoelectric element. When the charges quickly dissipate from the piezoelectric element, a time period during which the voltage detection circuit can detect a voltage of the piezoelectric element shortens.

It is therefore an object of the present invention to provide a piezoelectric element which increases a capacitance and includes a film partially including a piezoelectric resin and sandwiched between electrodes.

BRIEF SUMMARY OF THE INVENTION

A piezoelectric element according to one aspect of the present invention includes a first reference potential electrode, a piezoelectric film layered on top of the first reference potential electrode, and a signal electrode layered on top of the piezoelectric film. The combination of the first reference potential electrode, the piezoelectric film and the signal electrode form piezoelectric unit having a first capacitance. The piezoelectric film includes a piezoelectric resin.

A dielectric film is layered on top of the piezoelectric film, the dielectric layer having an insulation property. A second reference potential electrode layered on top of the dielectric film, the second potential electrode being electrically connected with the first reference potential electrode. The combination of the signal electrode, the dielectric film and the second reference potential electrode forming a capacitor having a second capacitance which is greater than the first capacitance. As used herein, the reference to layers being "on top" of one another is meant to indicate the relative orientation of the layers. For example, by turning the piezoelectric element upside down, the reference to being "on top" of another layer will be satisfied by the layer being below the other layer. Similarly, other orientations (e.g., sideways) will still have the relative orientation noted.

In the piezoelectric element according to an aspect of the present invention, the first reference potential electrode and the second reference potential electrode are electrically connected by a sensor unit or a detection circuit unit. A voltage detection circuit electrically connected to the first reference potential electrode and the signal electrode electrically functions as a complex element connected in parallel to a piezoelectric unit formed by sandwiching a film between the signal electrode and the first reference potential electrode and having piezoelectricity, and a capacitive element formed by sandwiching the dielectric film between the signal electrode and the second reference potential electrode.

In the piezoelectric element according to an aspect of the present invention, the piezoelectric unit having the piezoelectricity is electrically connected in parallel to the capacitive element having a larger capacitance than that of the piezoelectric unit, so that it is possible to increase the capacitance of the entire piezoelectric element. Consequently, the piezoelectric element according to the present invention can prevent the voltage of the piezoelectric element from becoming too high and being unable to be detected by the voltage detection circuit, the voltage of the piezoelectric element from being significantly influenced by noise superimposed on charges, and a time during which the voltage detection circuit can detect the voltage of the piezoelectric element from shortening.

The capacitance is proportional to a dielectric constant ε (F/m) between the electrodes and is inversely proportional to a distance between the electrodes. Hence, for example, the piezoelectric element is configured as follows to increase the capacitance.

The thickness of the dielectric film in the laminating direction is preferably less than the thickness of the film in the laminating direction, and a dielectric constant of the dielectric film is preferably greater than a dielectric constant of the film.

The signal electrode is preferably made of a copper (e.g., copper foil), and the first and second reference potential electrodes are preferably made of silver paste or a conductive non-woven fabric. When a bias is applied to the signal electrode, if the signal electrode is made of copper, the copper is hardly ionized as compared to silver, so that it is possible to prevent migration of the signal electrode. Further, while the piezoelectric resin may be a ferroelectric material such as PVDF (polyvinylidene fluoride), the piezoelectric resin may be polylactic acid.

The polylactic acid does not produce pyroelectricity unlike the ferroelectric material such as PVDF. Further, the polylactic acid does not need to be poled (polarization processing) and has light-transmissiveness, and therefore is better than PVDF.

When the polylactic acid is used as a piezoelectric film, the film may be a multilayer piezoelectric film formed by overlaying a first piezoelectric film and a second piezoelectric film in the laminating direction. A stretching direction of the first piezoelectric film may be identical to a stretching direction of the second piezoelectric film. One of the first and second piezoelectric films may be made of poly-L-lactic-acid and the other of the piezoelectric films may be made of poly-D-lactic-acid.

Poly-D-lactic-acid and poly-L-lactic-acid have a relationship of an enantiomer. The polylactic acid whose piezoelectricity derives from a molecule spiral structure makes directions in which charges are produced (referred to as charge directions below) reverse between PDLA and PLLA of the enantiomer. In this regard, the charge directions are directions from one principal surface in which negative charges are produced, to the other principal surface in which positive charges are produced in the film made of polylactic acid.

Thus, when the first and second films whose charge directions are reverse overlay one another, and the piezoelectric element stretches or contracts in a direction orthogonal to the laminating direction, charges are cancelled between the first and second piezoelectric films. When the piezoelectric element is curved in the laminating direction, the charge directions of the first and second piezoelectric films are aligned and the charges are added to each other. Thus, the piezoelectric element produces a potential difference between the signal electrode and the first reference potential electrode only when curved in the laminating direction (i.e., when the piezoelectric element is bent out of its plane).

The charge directions change according to not only a composition of polylactic acid but also the stretching direction of the piezoelectric film. More specifically, according to an aspect, the piezoelectric film may be a multilayer piezoelectric film formed by overlaying first and second piezoelectric films in which the stretching direction of the first piezoelectric film is orthogonal to the stretching direction of the second piezoelectric film, and both the first and second piezoelectric films are made of either poly-L-lactic-acid or poly-D-lactic-acid.

When the stretching directions are orthogonal to each other, orientation directions of molecules of polylactic acid of the first film and the second film are orthogonal to each other, and therefore the charge directions are reverse to each other.

Further, a bend detecting sensor which detects a bend includes a piezoelectric element which produces charges only when bent (curved) in the laminating direction (i.e., bent out of the plane of the piezoelectric element), and a circuit which detects a voltage of the piezoelectric element based on the charges retained by the piezoelectric element. The bend detecting sensor can be attached to, for example, a skin surface of a living body, to be used as a biosensor which detects a displacement in a normal direction of the skin surface.

In a piezoelectric element according to an aspect of the present invention, a dielectric film is sandwiched between a reference potential electrode and a signal electrode to form a capacitive element, and the capacitive element is electrically connected in parallel to a piezoelectric unit, so that the piezoelectric element can increase a capacitance of the entire piezoelectric element.

BRIEF EXPLANATION OF DRAWINGS

FIG. 2 is a side view illustrating a sensor element seen from a depth direction.

FIG. 4 is a side view of a sensor element according to a second embodiment seen from the depth direction.

FIG. 6(A) is a side view of the sensor element seen from the depth direction when a skin surface is stretched in a width direction.

FIG. 6(B) is a side view of the sensor element seen from the depth direction when the skin surface elevates in a height direction.

DESCRIPTION OF THE PREFERRED EMBODIMENTS

A biosensor 100 according to a first embodiment will be described with reference to FIGS. 1(A), 1(B) and 2. The biosensor 100 is typically attached to the surface of the skin of a living body to detect a displacement of the skin surface.

Figure 1A:
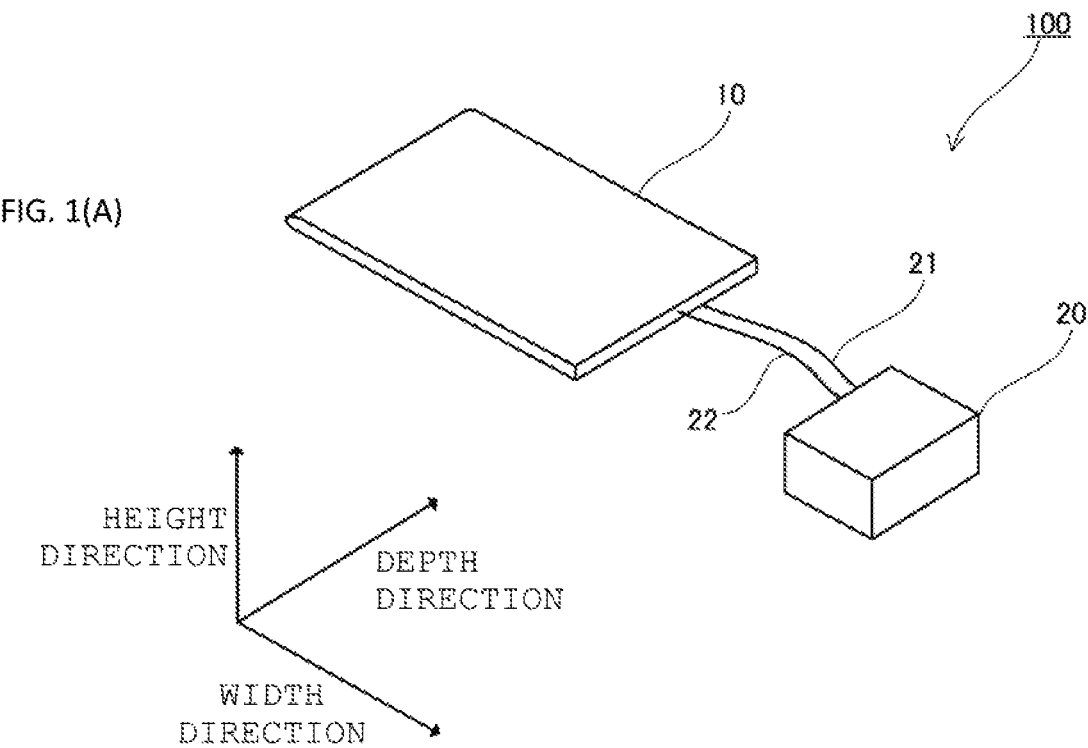
FIG. 1(A) is a perspective view of a biosensor according to a first embodiment.

As illustrated in FIG. 1(A), the biosensor 100 includes the sensor element 10 and a detecting unit 20. The sensor element 10 and the detecting unit 20 are electrically connected with signal lines 21 and 22 interposed therebetween. Alternatively, the detecting unit 20 may be directly connected to the sensor element 10 without the use of signal lines. The sensor element 10 has a film shape which is thin in a height direction as compared to a width and depth directions.

Figure 1B:
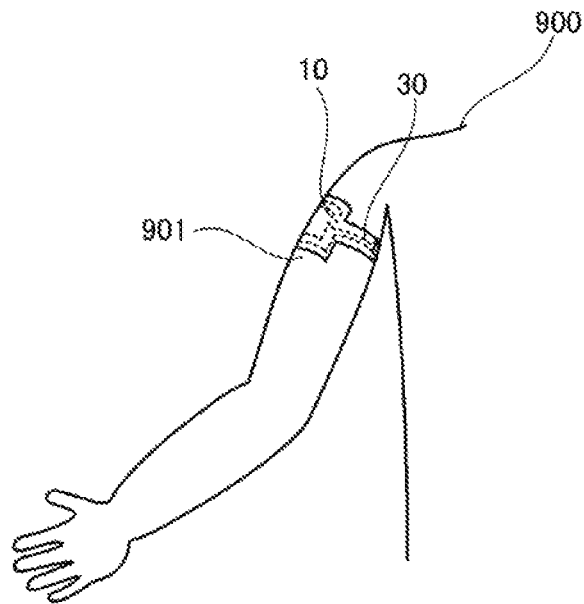
FIG. 1(B) is a view for explaining an exemplary use of the biosensor.

As illustrated in FIG. 1(B), the biosensor 100 is attached to a living body 900 such that an upper surface (a surface in the height direction as viewed in FIG. 1(A)) or a lower surface (a surface in a direction opposite to the height direction as viewed in FIG. 1(A))) of the sensor element 10 comes into contact with the surface of a skin 901 of the living body 900. The sensor element 10 can be attached to the living body 900 using, for example, a band 30 which sandwiches the sensor element 10 between the band 30 and the surface of the skin 901.

As illustrated in FIG. 2, the sensor element 10 preferably includes a reference potential electrode 5, a piezoelectric film 3, a signal electrode 2, a dielectric film 1 and a reference potential electrode 4. A respective adhesive layer (not shown) is preferably located between each electrode/film interface. In a preferred embodiment an insulation material (not shown), which insulates the reference potential electrode 4 and the reference potential electrode 5, is disposed at an outermost layer.

The signal electrode 2 is, for example, a thin film made of copper (Cu). An end portion of the signal electrode 2 in the width direction is electrically connected with the signal line 22.

The reference potential electrodes 4 and 5 are, for example, made of silver (Ag). Other metals such as copper (Cu), aluminum (Al), Indium tin oxide (ITO) or the like can also be used.

End portions of the reference potential electrodes 4 and 5 are electrically connected to one another by a connecting portion 6 interposed therebetween. The reference potential electrode 4, the reference potential electrode 5 and the connecting portion 6 are preferably formed by bending urethane films to which, for example, silver paste has been applied. The reference potential electrode 4, the reference potential electrode 5 and the connecting portion 6 may alternatively be formed, for example, by bending a conductive non-woven fabric. The right hand end portion of the reference potential electrode 5 (as viewed in FIG. 2) is electrically connected with a signal line 21.

The reference potential electrodes 4 and 5 may be electrically connected via a detection circuit (see FIG. 3) of the detecting unit 20 without the use of the connecting portion 6. When the reference potential electrodes 4 and 5 are electrically connected by the connecting portion 6, it is not necessary to provide separate signal lines for the reference potential electrodes 4 and 5. Thus, a connection failure of the signal line does not occur. Further, a configuration including the connecting portion 6 can easily and electrically connect the reference potential electrode 4 and the reference potential electrode 5 by bending the urethane film to which silver paste has been applied.

Furthermore, the length of the connecting portion 6 and the length of the signal electrode 2 in the depth direction are preferably equal, so that the signal electrode 2 is prevented from being influenced by external noise.

One side of either the reference potential electrode 4 or the reference potential electrode 5 is attached to the surface of the skin 901. The silver paste materials used to make the reference potential electrodes 4 and 5 preferably have a lower Young's moduli than that of a copper foil and therefore cause a greater distortion than a copper foil when the same stress is applied thereto. The sensor element 10 is formed by disposing the reference potential electrodes 4 and 5 made of silver paste which is distortable (relatively elastic), at the outermost layer and disposing the signal electrode 2 made of the copper foil which is hardly distorted (relatively inelastic), at the center. Consequently, the sensor element 10 is minimally stretched or contracted in the width and depth directions while being bendable in the height direction.

The piezoelectric film 3 is preferably made, partly or wholly, of polylactic acid which is a piezoelectric resin. For example, the piezoelectric film 3 may be formed by synthesizing a piezoelectric body and a resin.

The piezoelectric film 3 has piezoelectricity and therefore produces charges when distorted. The produced charges create a potential difference (e.g. several tens of volts) between the signal electrode 2 and the reference potential electrode 5.

The dielectric film 1 has an insulation property and insulates the reference potential electrode 4 from the signal electrode 2. The dielectric film 1 is preferably formed by, for example, applying an acrylic adhesive to opposite principal surfaces of a PET (Polyethylene terephthalate) base material. The dielectric film 1 is an example only, and an insulator film may be used instead of the dielectric film 1.

The thickness (in the height direction) of the dielectric film 1 is preferably smaller than the thickness of piezoelectric film 3 as illustrated in FIG. 2. A dielectric constant ε (F/m) of the dielectric film 1 is preferably higher than a dielectric constant of the piezoelectric film 3. Hence, a capacitance $C_A$ formed between the signal electrode 2 and the reference potential electrode 4 is larger than a capacitance $C_B$ formed between the signal electrode 2 and the reference potential electrode 5.

Alternatively, the dielectric film 1 may not have a higher dielectric constant ε and a smaller thickness than those of the piezoelectric film 3. The thickness and the dielectric constant ε of the dielectric film 1 may be optionally set such that the capacitance CA formed between the signal electrode 2 and the reference potential electrode 4 is larger than the capacitance $C_B$ formed between the signal electrode 2 and the reference potential electrode 5.

Figure 3:
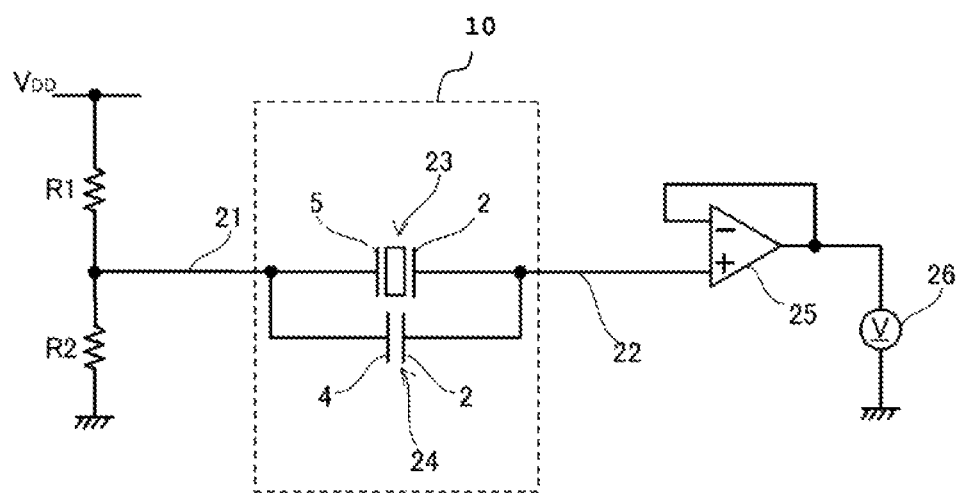
FIG. 3 is a view illustrating a circuit example of the biosensor.

Next, FIG. 3 is a view illustrating a circuit example of the biosensor 100. In the detecting unit 20, a voltage detection circuit which detects a potential difference between the signal electrode 2 and the reference potential electrode 5 of the sensor element 10 is configured.

As illustrated in FIG. 3, the voltage detection circuit includes a piezoelectric unit 23, a capacitor 24, an operational amplifier 25, and a voltage detector 26.

The piezoelectric unit 23 is realized by sandwiching the piezoelectric film 3 between the signal electrode 2 and the reference potential electrode 5 in the sensor element 10. The piezoelectric unit 23 is biased by a voltage VD whose value is determined by the drive voltage VDD and the voltage divider circuit defined by resistors R1 and R2.

More specifically, the reference potential electrode 5 is electrically connected to the junction between resistors R1 and R2 by the signal line 21. The signal electrode 2 is electrically connected to a positive input terminal of the operational amplifier 25 by the signal line 22.

The capacitor 24 is realized by sandwiching the dielectric film 1 between the signal electrode 2 and the reference potential electrode 4. The capacitor 24 is also biased by the voltage VD. More specifically, the reference potential electrode 4 is electrically connected to the junction between resistors R1 and R2 by the signal line 21.

As a result, the capacitor 24 is electrically connected in parallel to the piezoelectric unit 23. Consequently, the capacitance CT of the sensor element 10 (which is equal to $C_A + C_B$) is higher than it would be if it only included the piezoelectric unit 23.

The operational amplifier 25 constitutes a voltage follower circuit. That is, a negative input terminal of the operational amplifier 25 is electrically connected to an output terminal of the operational amplifier 25. Thus, the operational amplifier 25 outputs (from the output terminal) a voltage equal to a voltage inputted to its positive input terminal in a state where an impedance seen from the piezoelectric unit 23 and the capacitor 24 is increased. The operational amplifier 25 is preferably powered by the drive voltage VDD (this connection is not shown in the Figure).

The output terminal of the operational amplifier 25 is electrically connected to the voltage detector 26 which detects the potential of the output terminal of the operational amplifier 25 with respect to a ground potential.

When the piezoelectric unit 23 produces charges, produced charges Q are stored by both the piezoelectric unit 23 and the capacitor 24. The charges Q retained by the piezoelectric unit 23 and the capacitor 24 produce potential differences between the signal electrode 2 and the reference potential electrode 4 and between the signal electrode 2 and the reference potential electrode 5. A potential Vdiff of the signal electrode 2 with respect to a potential of the reference potential electrode 4 is inversely proportional to a capacitance CT of the entire sensor element 10 and is proportional to the quantity of the charges Q produced by the piezoelectric unit 23. That is, the potential Vdiff can be calculated according to a following equation.

$$Vdiff=Q/(C_A+C_B)$$

Even when noise is superimposed on the charges Q retained by the piezoelectric unit 23 and the capacitor 24, since the capacitance CT of the sensor element 10 is larger than it would be if it included only the piezoelectric unit 23, it can better suppress an influence of noise on the potential difference Vdiff. Further, the potential Vdiff of the sensor element 10 does not become too high since the capacitance CT of the entire sensor element 10 is higher than it would be if the sensor element only contained the piezoelectric unit 23.

The charges Q retained by the piezoelectric unit 23 and the capacitor 24 gradually dissipate over time, and this dissipation is slower than in the prior art since a time constant τ is proportional to the capacitance CT, which is higher than it would otherwise be if the sensor element only included the piezoelectric unit 23. Consequently, the biosensor 100 can extend the time during which the voltage detector 26 can detect a voltage (because it slows down the dissipation of charges from the sensor element 10).

Further, the capacitor 24 can effectively cancel noise produced near the sensor element 10 as compared to a case where noise of the charges Q is cancelled outside the sensor element 10. Particularly, the sensor element 10 is suitably configured to detect a fluctuation of a low frequency (e.g. 1 Hz) signal such as a pulse signal to remove noise inside the sensor element 10.

Further, copper which is preferably used to make the signal electrode 2 is ionized to a much lower degree than it would be if the sensor element only included the piezoelectric unit 23 and causes minimal migration. Consequently, even when the signal electrode 2 is biased at a voltage corresponding to the drive voltage VDD, the sensor element 10 can suppress deterioration of the signal electrode 2 due to migration.

The piezoelectric film 3 is not limited to polylactic acid and may be made of polyvinylidene fluoride (PVDF). Polylactic acid does not provide a pyroelectric effect unlike ferroelectric polymer such as polyvinylidene fluoride. Hence, the piezoelectric film 3 whose material is polylactic acid and is suitable to constitute the sensor element 10 to which a temperature of the living body transmits. Further, the piezoelectric film 3 made of polylactic acid has light-transmissiveness. Therefore, when other components such as the signal electrode 2 and the reference potential electrode 5 are formed by using a light-transmissive material, it is possible to make the entire sensor element 10 transparent and make the surface of the skin 901 visible with the sensor element 10 attached to the skin surface.

Further, the voltage detection circuit is not limited to the circuit example illustrated in FIG. 3, and may be any circuit which can detect a change in voltage based on charges produced by the sensor element 10. For example, the voltage detection circuit may be a circuit (such as a circuit used for a bias condenser microphone) which includes a FET whose output voltage of a drain rises according to a quantity of charges retained by the piezoelectric unit 23 and the capacitor 24.

Figure 5A:
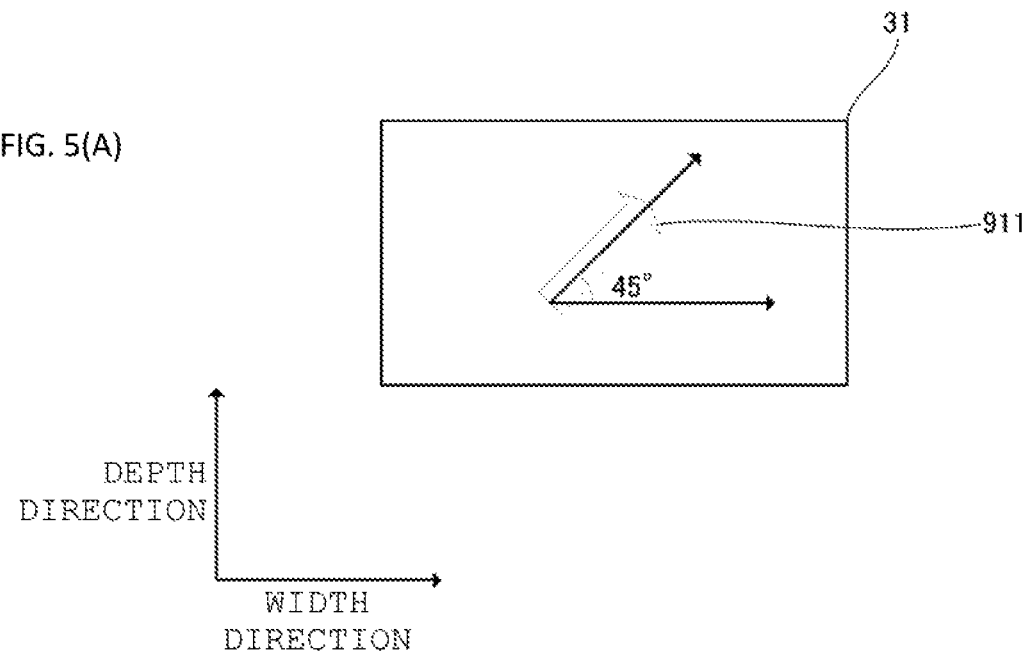
FIG. 5(A) is a top view of a first film.
Figure 5B:
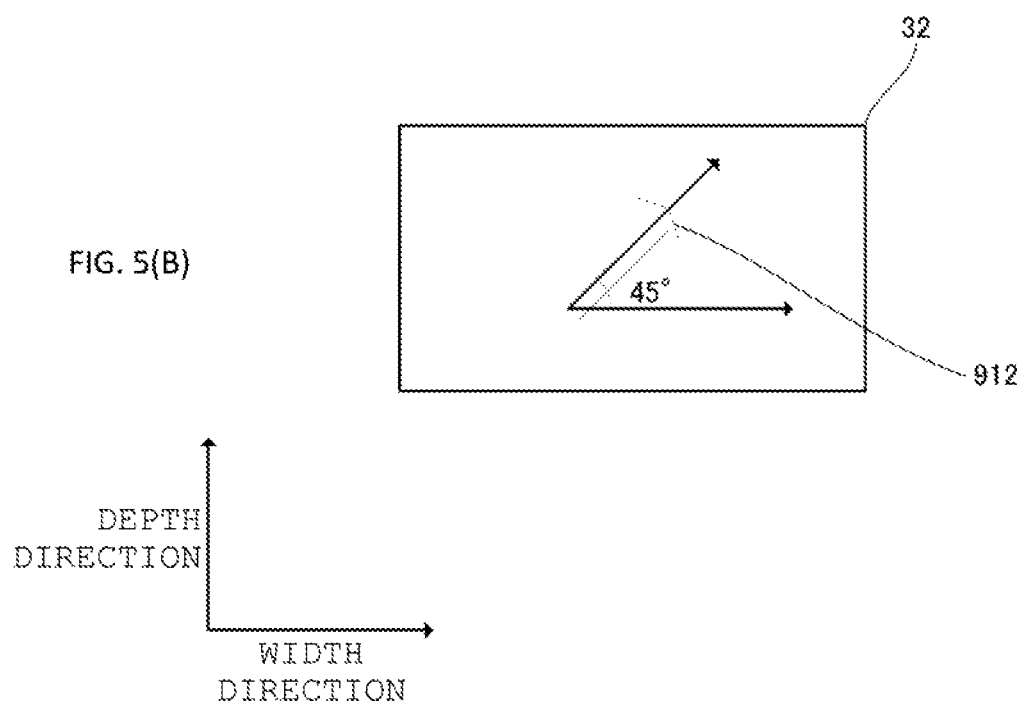
FIG. 5(B) is a top view of a second film.

Next, a sensor element 10A according to a second embodiment will be described with reference to FIGS. 4, 5(A), and 5(B). FIG. 4 is a side view illustrating the sensor element 10A seen from a depth direction. FIG. 5(A) is a top view of a piezoelectric film 31 (corresponding to a first film), and FIG. 5(B) is a top view of a piezoelectric film 32 (corresponding to a second film).

The sensor element 10A does not produce charges when stretched or contracted in a planar direction (a width direction and the depth direction), and produces charges only when curved in a laminating direction. More specifically, the sensor element 10A differs from a sensor element 10 in that a piezoelectric film 3A is formed by two piezoelectric film layers 31 and 32.

The piezoelectric films 31 and 32 are made of polylactic acid having different compositions. The piezoelectric film 31 is preferably made of Poly-D-Lactic-Acid (PDLA), and the piezoelectric film 32 is preferably made of Poly-L-Lactic-Acid (PLLA). The order of those films can be reversed.

Orientation directions of molecules of polylactic acid of the piezoelectric films 31 and 32 are the same. The orientation directions of the molecules of polylactic acid are the directions in which the films are stretched. More specifically, the piezoelectric film 31 is stretched in a counterclockwise direction by 45° from the width direction as indicated by an outlined arrow 911 in FIG. 5(A). The piezoelectric film 32 is stretched in the same direction as the stretching direction of the piezoelectric film 31 as indicated by an outlined arrow 912 in FIG. 5(B). In this regard, the width direction and the stretching direction of the films 31 and 32 may be nearly 45° and can produce a charge production effect even in a range of, for example, 35° to 55°.

PDLA and PLLA have a relationship of an enantiomer. Hence, the piezoelectric films 31 and 32 are made of polylactic acid of the mutual enantiomers and orientation directions of molecules of polylactic acid are the same. Therefore, directions (referred to as charge directions below) of polarities of charges produced when the same distortion is produced are reverse.

For example, coextrusion is used to prepare the piezoelectric film 31 made of PDLA and the piezoelectric film 32 made of PLLA as a laminated layer. In the coextrusion, an extruder of melted PLLA and an extruder of melted PDLA are overlaid and the PLLA and the PDLA are simultaneously extruded to a circumferential surface of a rotating cooling drum such that the extruded resin forms a laminated layer. Thus, the piezoelectric films 31 and 32 are integrally formed without an adhesive layer, so that it is possible to suppress an increase in the thickness. While this is the preferred structure, the piezoelectric film 31 and the piezoelectric film 32 may instead be adhered to one another using an adhesive.

A function of the sensor element 10A will be described with reference to FIGS. 6(A) and 6(B). FIG. 6(A) is a side view of the sensor element 10A seen from the depth direction when a surface of a skin 901 is stretched in the width direction, and FIG. 6(B) is a side view of the sensor element 10A seen from the depth direction when the surface of the skin 901 elevates in a height direction. The reference potential electrodes 4 and electrode 5 are omitted from FIGS. 6(a) and 6(B) for ease of explanation.

As illustrated in FIG. 6(A), when the surface of the skin 901 is stretched in the width direction, the films 31 and 32 are stretched in the width direction. Charges produced by the piezoelectric film 31 are cancelled by charges produced by the piezoelectric film 32 since charge directions of the piezoelectric film 31 and the piezoelectric film 32 are opposed to one another as indicated schematically by arrows 801 and 802.

Similarly, even when the surface of the skin 901 is contracted in the width direction, the charges produced by the piezoelectric film 31 are cancelled by the charges produced by the piezoelectric film 32. In addition, when the surface of the skin 901 is stretched in the depth direction (into the page in the figures), the charges produced by the piezoelectric film 31 are cancelled by the charges produced by the piezoelectric film 32.

As illustrated in FIG. 6(B), when the surface of the skin 901 elevates in the height direction, the piezoelectric film 31 is stretched with respect to the piezoelectric film 32. For this reason, the charges produced by the piezoelectric film 31 are added to the charges produced by the piezoelectric film (shown schematically by arrows 811 and 812) 32 since the charge directions of the piezoelectric film 31 and the piezoelectric film 32 are reverse. Then, the voltage detector 26 (FIG. 3) of a voltage detection circuit detects a voltage corresponding to charges added by the films 31 and 32. In addition, when the surface of the skin 901 sinks in a direction opposite to the height direction, the charges produced by the piezoelectric film 31 are added to the charges produced by the piezoelectric film 32.

The sensor element 10A produces substantially no charges between a signal electrode 2 and the reference potential electrode 4 even when the surface of the skin 901 stretches and contracts in the planar direction (the width direction and the depth direction) but can produce charges between the signal electrode 2 and the reference potential electrode 5 only when the surface of the skin 901 elevates or sinks in the height direction.

In addition, the piezoelectric film 31 and the piezoelectric film 32 may be reversely disposed in the sensor element 10A.

The sensor element 10A described above includes the two films 31 and 32 whose compositions of polylactic acid are made to differ to make their charge directions reverse. Alternatively, the sensor element 10A may include two films whose orientation directions of molecules of polylactic acid are made to differ as follows to make the charge directions reverse.

Figure 7:
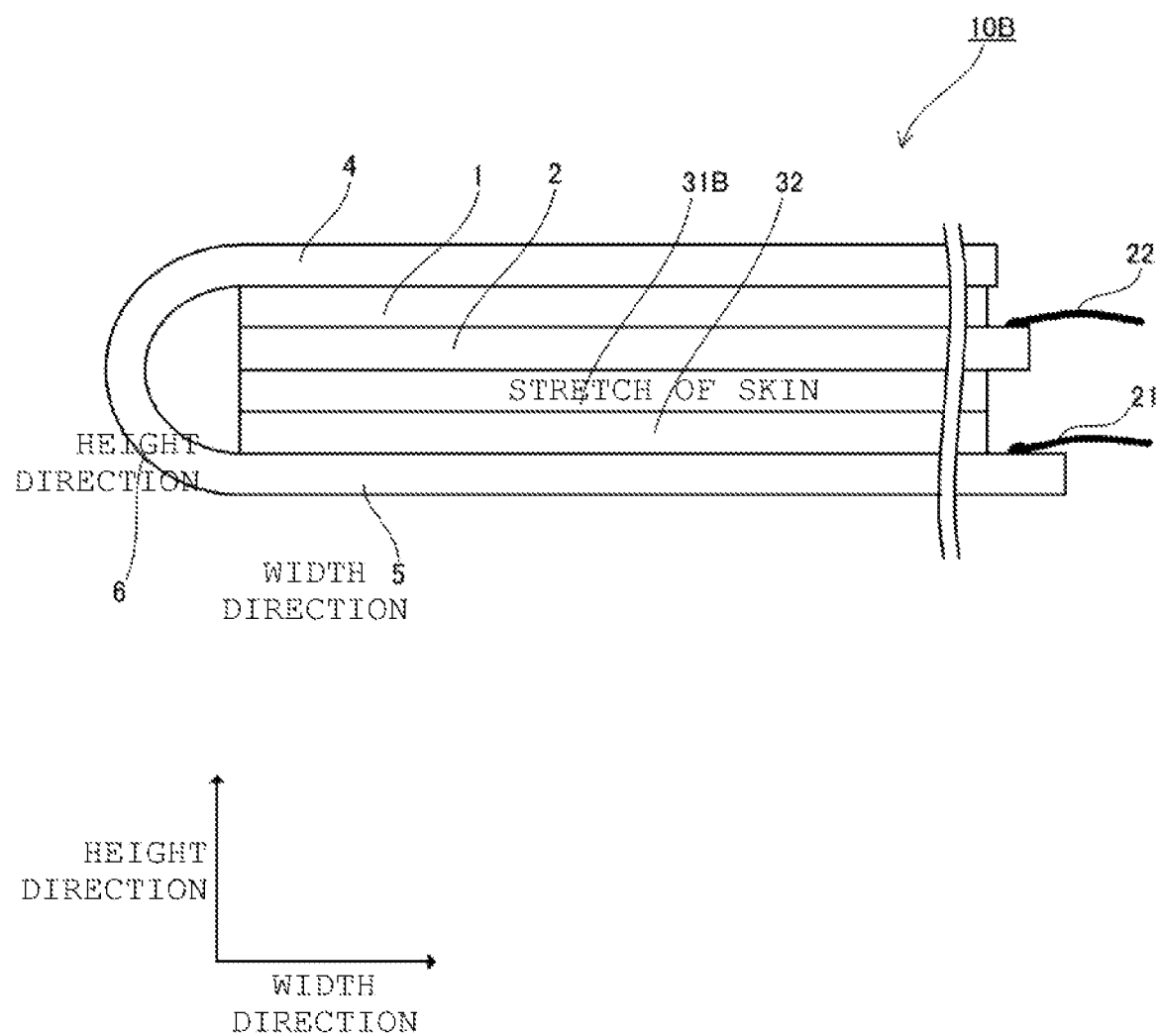
FIG. 7 is a side view of the sensor element according to the second embodiment seen from the depth direction.
Figure 8:
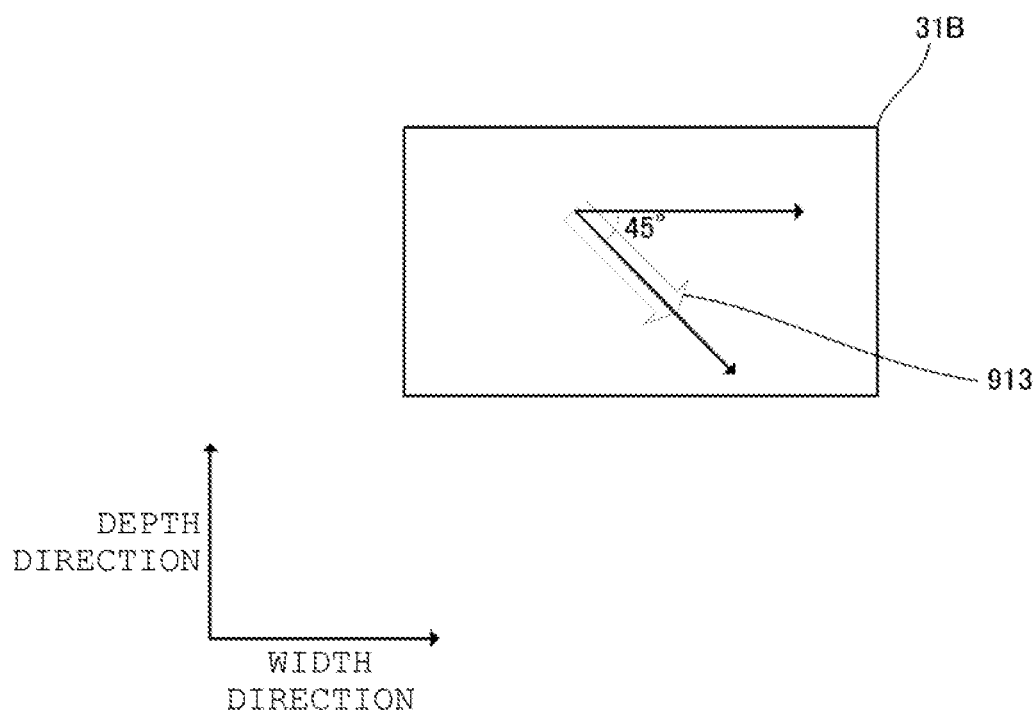
FIG. 8 is a top view of the second film.

FIG. 7 is a side view of a sensor element 10B according to a third embodiment seen from a depth direction. FIG. 8 is a top view of a piezoelectric film 31B.

The sensor element 10B differs from the sensor element 10 in that it includes the piezoelectric film 31B instead of the piezoelectric film 31. Components which overlap with components of the sensor element 10 will not be described.

The piezoelectric film 31B is preferably made of PLLA. The piezoelectric film 31B is stretched in a clockwise direction by 45° with respect to a width direction as indicated by an outlined arrow 913 in FIG. 8. Thus, the PLLA included in the piezoelectric film 31B is oriented in the clockwise direction by 45° from the width direction. Hence, the piezoelectric film 31B and a piezoelectric film 32 have orientation directions of molecules of polylactic acid which are orthogonal to each other and are made of the same composition, and therefore have reverse charge directions.

In this regard, the sensor element 10B includes the piezoelectric film 31B and the piezoelectric film 32 made of PLLA. However, the sensor element 10B may include two films made of PDLA and the two films may be disposed such that orientation directions of molecules of polylactic acid are orthogonal to each other according to an aspect.

The invention claimed is:

1. A piezoelectric element, comprising:
a first reference potential electrode;
a piezoelectric film layered on top of the first reference potential electrode, the piezoelectric film including a piezoelectric resin;
a signal electrode layered on top of the piezoelectric film, the combination of the first reference potential electrode, the piezoelectric film and the signal electrode forming piezoelectric unit having a first capacitance;
a dielectric film layered on top of the piezoelectric film, the dielectric layer having an insulation property; and
a second reference potential electrode layered on top of the dielectric film, the second potential electrode being electrically connected with the first reference potential electrode, the combination of the signal electrode, the dielectric film and the second reference potential electrode forming a capacitor having a second capacitance which is greater than the first capacitance.

2. The piezoelectric element according to claim 1, wherein:
the first reference potential electrode, the piezoelectric film, the signal electrode, the dielectric film and the second reference potential electrode are stacked in a laminating direction;
a thickness of the thickness of the dielectric film in the laminating direction is less than a thickness of the film in the laminating direction, and
a dielectric constant of the dielectric film is greater than a dielectric constant of the piezoelectric film.

3. The piezoelectric element according to claim 1, wherein:
the signal electrode is made of copper, and
the first and second reference potential electrodes are made of silver.

4. The piezoelectric element according to claim 1, wherein the piezoelectric resin is polylactic acid.

5. The piezoelectric element according to claim 4, wherein:
the first reference potential electrode, the piezoelectric film, the signal electrode, the dielectric film and the second reference potential electrode are stacked in a laminating direction;
the piezoelectric film is a multilayer film comprising first and second piezoelectric films layered on top of one another in the laminating direction,
a stretching direction of the first film is identical to a stretching direction of the second film; and
one of the first film and the second film is made of poly-L-lactic-acid, and the other one of the first film and the second film is made of poly-D-lactic-acid.

6. The piezoelectric element according to claim 4, wherein:
the first reference potential electrode, the piezoelectric film, the signal electrode, the dielectric film and the second reference potential electrode are stacked in a laminating direction;
the piezoelectric film is a multilayer film comprising first and second piezoelectric films layered on top of one another in the laminating direction;
a stretching direction of the first piezoelectric film is orthogonal to a stretching direction of the second piezoelectric film, and
one of the first and second piezoelectric films being made of poly-L-lactic-acid, the other of the piezoelectric films being made of poly-D-lactic-acid.

7. The piezoelectric element according to claim 1, wherein the piezoelectric film is a multilayer piezoelectric film comprising first and second piezoelectric films layered on top of one another in a plane, the characteristics of the first and second piezoelectric films being such that they only generate net charges when the first and second piezoelectric films are distorted outside of the plane.

8. The piezoelectric element according to claim 7, wherein the first and second piezoelectric films generate charges which cancel one another when the films are stretched and/or contracted within the plane.

9. The piezoelectric element according to claim 7, wherein the first and second piezoelectric films have the relationship of an enantiomer.

10. The piezoelectric element according to claim 7, wherein the first and second piezoelectric films are formed of the same material but have orthogonal orientations.

11. A bend detecting sensor, comprising:
(a) a piezoelectric element including:
a first reference potential electrode;
a piezoelectric film layered on top of the first reference potential electrode, the piezoelectric film including a piezoelectric resin;
a signal electrode layered on top of the piezoelectric film, the combination of the first reference potential electrode, the piezoelectric film and the signal electrode forming piezoelectric unit having a first capacitance;
a dielectric film layered on top of the piezoelectric film, the dielectric layer having an insulation property; and
a second reference potential electrode layered on top of the dielectric film, the second potential electrode being electrically connected with the first reference potential electrode, the combination of the signal electrode, the dielectric film and the second reference potential electrode forming a capacitor having a second capacitance; and
(b) a detection circuit which detects a voltage of the piezoelectric element based on a charge retained in the piezoelectric element.

12. The bend detecting sensor according to claim 11, wherein:
the first reference potential electrode, the piezoelectric film, the signal electrode, the dielectric film and the second reference potential electrode are stacked in a laminating direction;
a thickness of the thickness of the dielectric film in the laminating direction is less than a thickness of the film in the laminating direction, and
a dielectric constant of the dielectric film is greater than a dielectric constant of the piezoelectric film.

13. The bend detecting sensor according to claim 11, wherein:
the signal electrode is made of copper, and
the first and second reference potential electrodes are made of silver.

14. The bend detecting sensor according to claim 11, wherein the piezoelectric resin is polylactic acid.

15. The bend detecting sensor according to claim 14, wherein:
the first reference potential electrode, the piezoelectric film, the signal electrode, the dielectric film and the second reference potential electrode are stacked in a laminating direction;
the piezoelectric film is a multilayer film comprising first and second piezoelectric films layered on top of one another in the laminating direction,
a stretching direction of the first film is identical to a stretching direction of the second film; and
one of the first film and the second film is made of poly-L-lactic-acid, and the other one of the first film and the second film is made of poly-D-lactic-acid.

16. The bend detecting sensor according to claim 14, wherein:
the first reference potential electrode, the piezoelectric film, the signal electrode, the dielectric film and the second reference potential electrode are stacked in a laminating direction;
the piezoelectric film is a multilayer film comprising first and second piezoelectric films layered on top of one another in the laminating direction;
a stretching direction of the first piezoelectric film is orthogonal to a stretching direction of the second piezoelectric film, and
one of the first and second piezoelectric films being made of poly-L-lactic-acid, the other of the piezoelectric films being made of poly-D-lactic-acid.

17. The bend detecting sensor according to claim 11, wherein the piezoelectric film is a multilayer piezoelectric film comprising first and second piezoelectric films layered on top of one another in a plane, the characteristics of the first and second piezoelectric films being such that they only generate net charges when the first and second piezoelectric films are distorted outside of the plane.

18. The bend detecting sensor according to claim 17, wherein the first and second piezoelectric films generate charges which cancel one another when the films are stretched and/or contracted within the plane.

19. The bend detecting sensor according to claim 17, wherein the first and second piezoelectric films have the relationship of an enantiomer.

20. The bend detecting sensor according to claim 17, wherein the first and second piezoelectric films are formed of the same material but have orthogonal orientations.

* * * * *